(12) United States Patent
Trimmer (10) Patent No.: US 6,520,477 B2
(45) Date of Patent: Feb. 18, 2003

(54) MICRO PUMP

(76) Inventor: William Trimmer, 58 Riverview Ter., Belle Mead, NJ (US) 08502

( * ) Notice: Subject to any disclaimer, the term of this patent is extended or adjusted under 35 U.S.C. 154(b) by 66 days.

(21) Appl. No.: 09/775,400

(22) Filed: Feb. 1, 2001

(65) Prior Publication Data

US 2002/0103412 A1 Aug. 1, 2002

(51) Int. Cl.⁷ .............................................. F16K 31/02
(52) U.S. Cl. ............... 251/11; 251/129.01; 251/129.06; 251/331; 216/2; 604/246
(58) Field of Search .......................... 604/246; 251/11, 251/129.01, 129.06, 331; 216/2

(56) References Cited

U.S. PATENT DOCUMENTS 4,923,444 A * 5/1990 Daoud et al. ............... 604/131
6,129,331 A * 10/2000 Henning et al. ............... 251/11
6,168,395 B1 * 1/2001 Quenzer et al. ....... 251/129.01

* cited by examiner

Primary Examiner—Philippe Derakshani
(74) Attorney, Agent, or Firm—Christie, Parker & Hale, LLP (57) ABSTRACT

This invention is directed to a microelectromechanical valve having two or more diaphragms containing non-aligned holes to control the flow of fluids. Fluid flows through the holes in the first diaphragm and then must flow between the first and second diaphragm to reach the holes in the second diaphragm, whereupon the fluid is free to flow past the second diaphragm.

68 Claims, 8 Drawing Sheets

MICRO PUMP

FIELD OF THE INVENTION

The present invention relates generally to the control and pumping of liquids and gasses, hereafter called fluids, in very small regions, and more particularly to micro valves and micro pumps.

BACKGROUND OF THE INVENTION

It is useful to control fluids in small regions. For example, micro pumps that can be implanted under the skin for the delivery of medicine for patients or the manipulation of pressurized fluids to control micro surgical instruments used in endoscopic and labrascopic surgery, or the fluidic control of micro chromatography systems used to detect undesirable elements in the environment or for controlling samples such as blood and chemical reagents to build a complete analytical system that can perform analysis in a physician's office or in the field, or for controlling the flow of small particles or devices entrained in a fluid, or for use as a controller for a microair table to float and move devices, or as a rapid acting fluidic switch that can control larger valves that control the flow of larger amounts of fluids.

These devices can be made by a variety of micro fabrication methods, including silicon fabrication techniques such as silicon surface machining and silicon bulk machining and wafer bonding and etching and deposition and also with non-silicon fabrication technologies such as LIGA (German for Lithographie, Galvanoformung, and Abformung or in English X-ray lithography, electroforming and molding processes) or EDM machining (Electro Discharge Machining) or plating or molding or stereolithography or a number of other technologies familiar to researchers in the field of micro fabrication.

Micro valves tend to leak because it is difficult to form a good micro valve seat. As the valve gets smaller, there is less material in the valve seat, and it is quite easy to scratch or crush one of these micro valve seats. Further, current micro valves have limited application because they are not capable of regulating fluid flows at high pressures.

Thus, there is a need for a micro valve having a good micro valve seat, and further, being capable of regulating fluid flows exerting high pressure loads.

SUMMARY OF THE INVENTION

The present invention is directed to a microelectromechanical valve having two or more diaphragms containing non-aligned holes to control the flow of fluids. Fluid flows through the holes in the first diaphragm and then must flow between the first and second diaphragm to reach the holes in the second diaphragm, whereupon the fluid is free to flow past the second diaphragm.

In a presently preferred embodiment, valve comprises a first diaphragm in spaced opposed relationship to a second diaphragm. The diaphragms comprise offsetting holes such that fluid flow between the diaphragms is impeded when the diaphragms are in close proximity to one another and fluid flow through the diaphragms is enabled when the diaphragms are spaced apart, and an actuator for causing the diaphragms to approach and retract relative to each other.

BRIEF DESCRIPTION OF THE DRAWINGS

These and other features and advantages of the present invention will be better understood by reference to the following detailed description when considered in conjunction with the accompanying drawings herein.

DETAILED DESCRIPTION OF THE INVENTION

Figure 1:
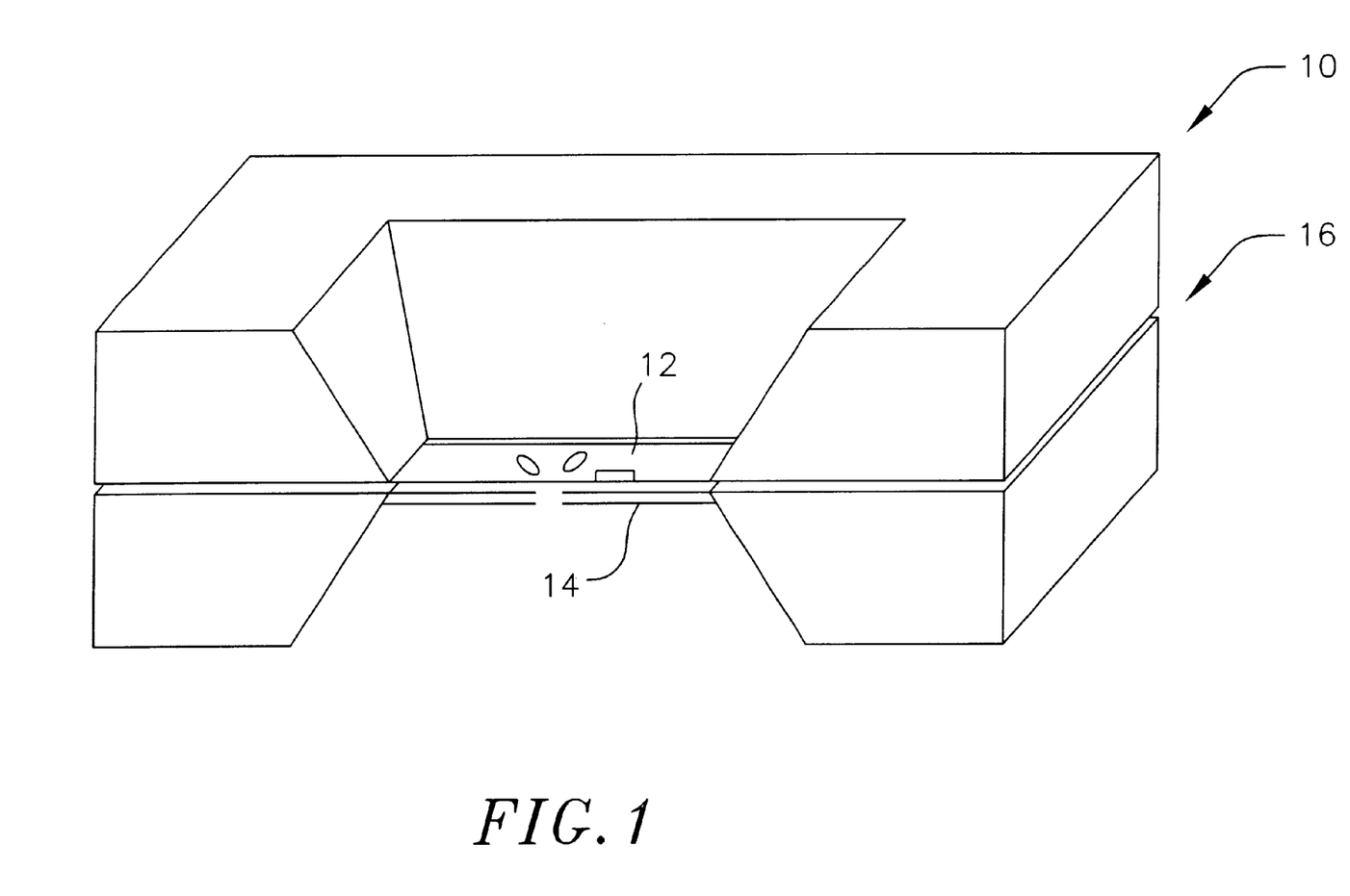
FIG. 1 is a perspective view of a microelectro valve according to the present invention.

The present invention, as shown in FIG. 1, provides a valve 10 having two or more diaphragms in a proximally spaced relationship. Each of the diaphragms contain a series of holes. The holes of each of the diaphragms are offset with respect to each other to control the flow of fluids through the valve. In a preferred embodiment, fluid flows through the holes in a first diaphragm 12 and into a space or channel 16 between the first and a second diaphragm 14 to reach the holes in the second diaphragm, where upon the fluid is free to flow past the second diaphragm.

Figure 2A:
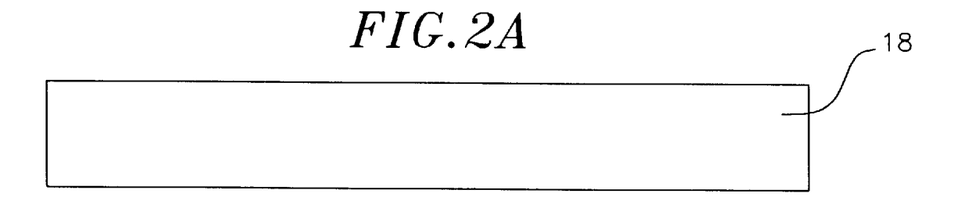
FIGS. 2A–2F are elevation views of a silicon wafer during the various processing steps resulting in a flexible perforated diaphragm used as one portion of the valve according to the present invention.
Figure 2B:
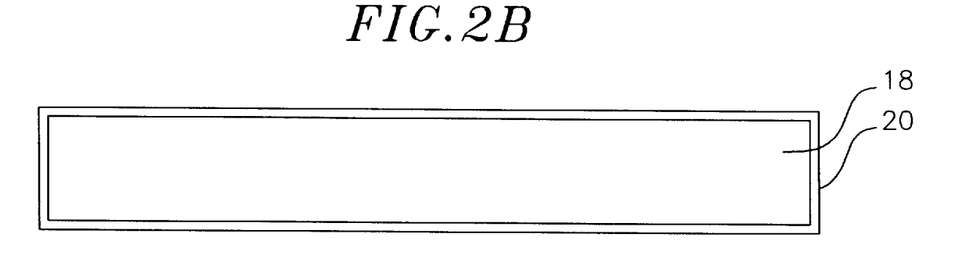
Figure 2C:
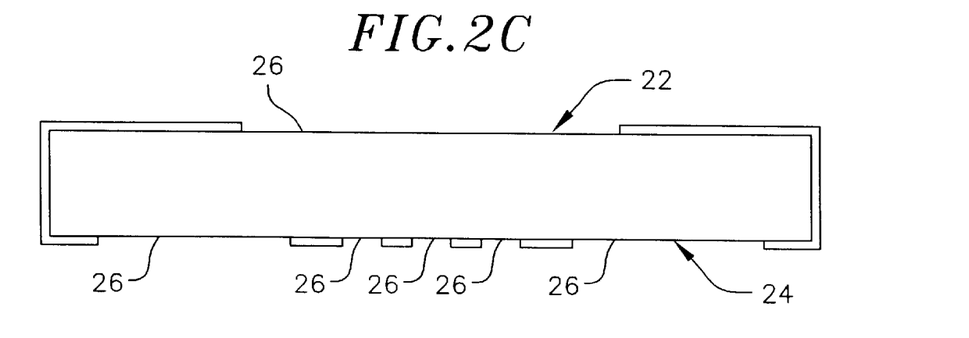
Figure 2D:
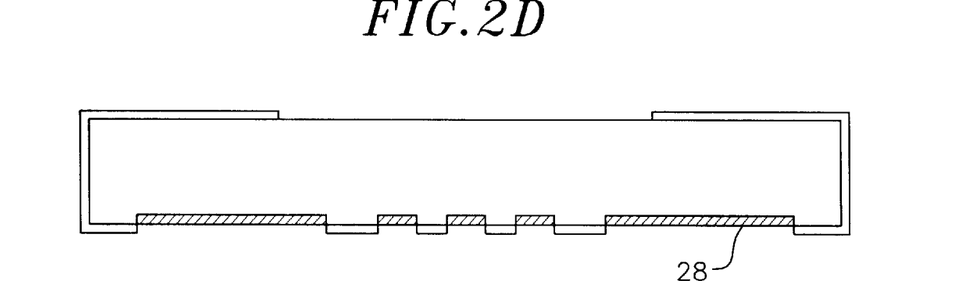

In a first preferred embodiment, the first and second diaphragms 12 and 14 are two silicon wafers 18 that are bonded to form the micro valve 10. Initially the silicon wafer shown in FIG. 2A is oxidized and coated with a layer of silicon nitride 20 on both sides, as shown in FIG. 2B. In alternative embodiments, the silicon wafer may be coated with other photoresist material, such as diamond-like carbon, silicon dioxide and silicon carbide. Top and bottom surfaces 22 and 24 of the wafer 18 are patterned using photolithography and etching to create a series of openings 26 in the silicon nitride and thermal oxide layer as shown in FIG. 2C. The bottom of the wafer is diffused with boron to penetrate the wafer and create an etchant impermeable bottom surface layer 28 as shown in FIG. 2D. The boron only penetrates the wafer at areas of the wafer exposed by the openings 26 and does not penetrate the wafer where the photoresist, which in this embodiment is the silicon nitride, is not removed.

Figure 2E:
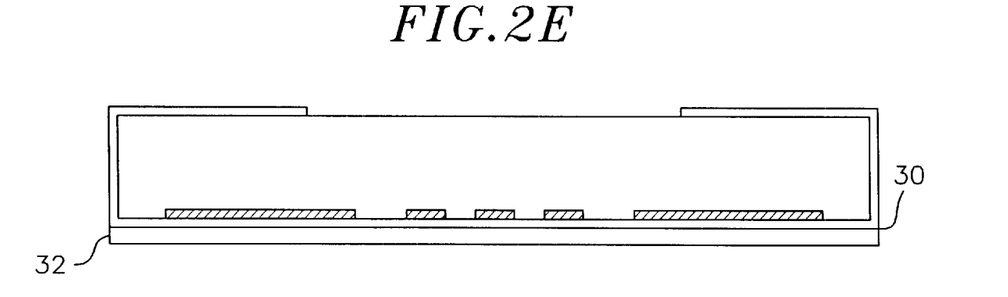

Referring to FIG. 2E, after the bottom of the wafer is diffused with boron, a conductive layer 30, preferably comprising fluorine or metals, such as aluminum, titanium-platinum-gold, or chrome, is deposited on the bottom layer of silicon nitride. The conductive layer 30 is then patterned and coated with a second layer 32 of silicon nitride.

Figure 2F:
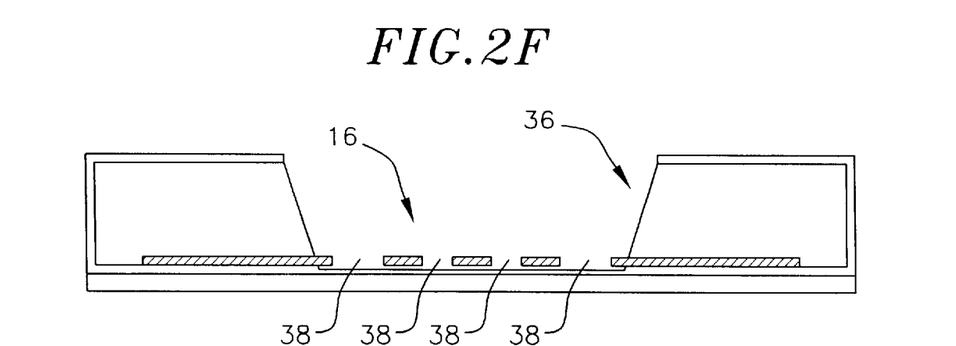

As shown in FIG. 2F, wafer is finally formed by etching the top portion of the wafer with potassium hydroxide (KOH) or similar anisotropic etchant, such as potassium hydroxide, ethylene diamine or hydrazine. The etched portion of the wafer forms a tapered cavity 36 extending between the top and bottom surfaces 22 and 24 of the wafer, thus etching away a central portion of the wafer to form a thin diaphragm 35 comprising the conductive layer 30 and the second silicon nitride layer 32 having a plurality of holes 38 located therein between the impermeable portions of the bottom layer, whereby fluid may pass though the diaphragm.

Figure 3:
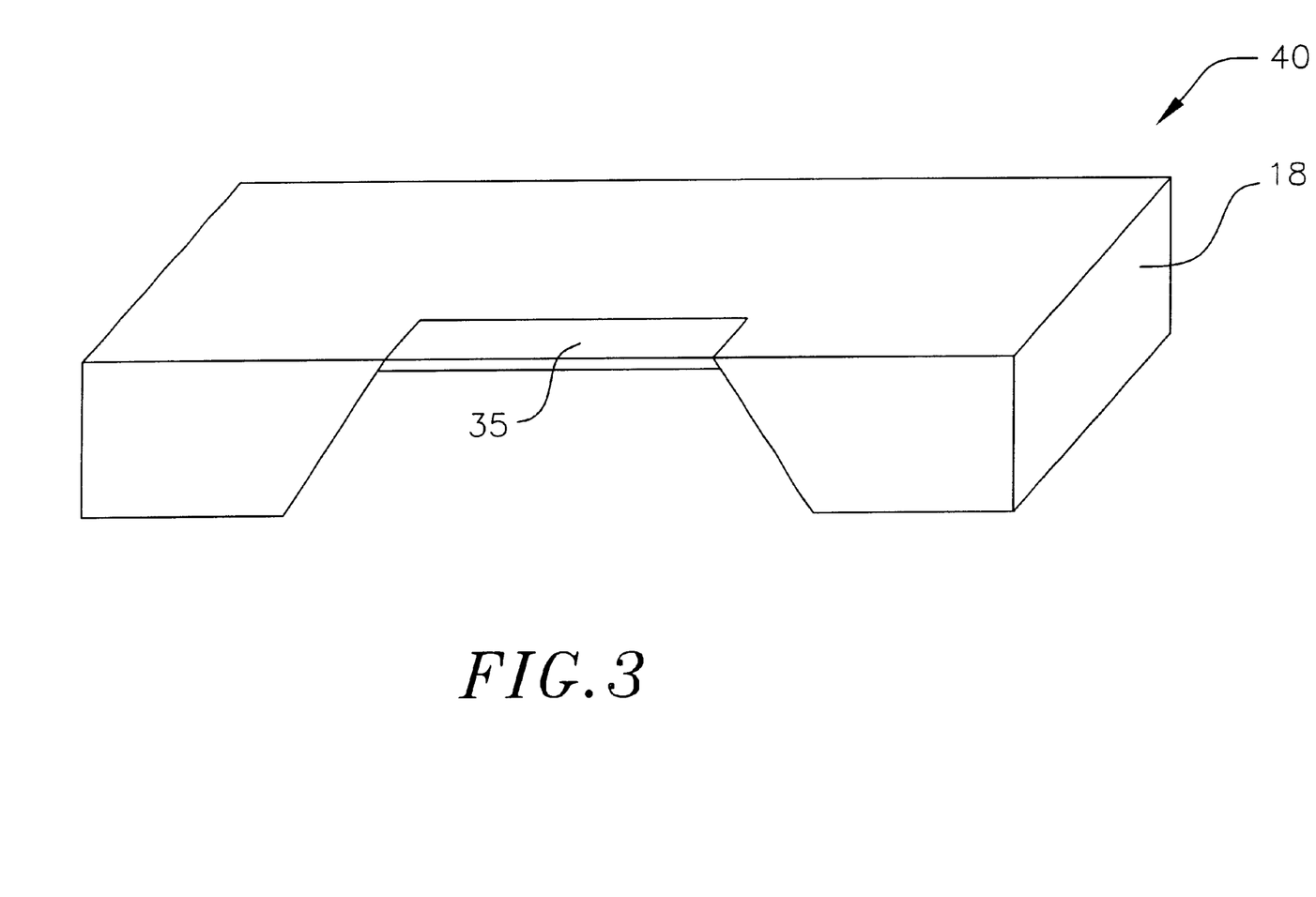
FIG. 3 is a perspective view of a valve half produced by the steps of FIGS. 2A–2F.
Figure 4:
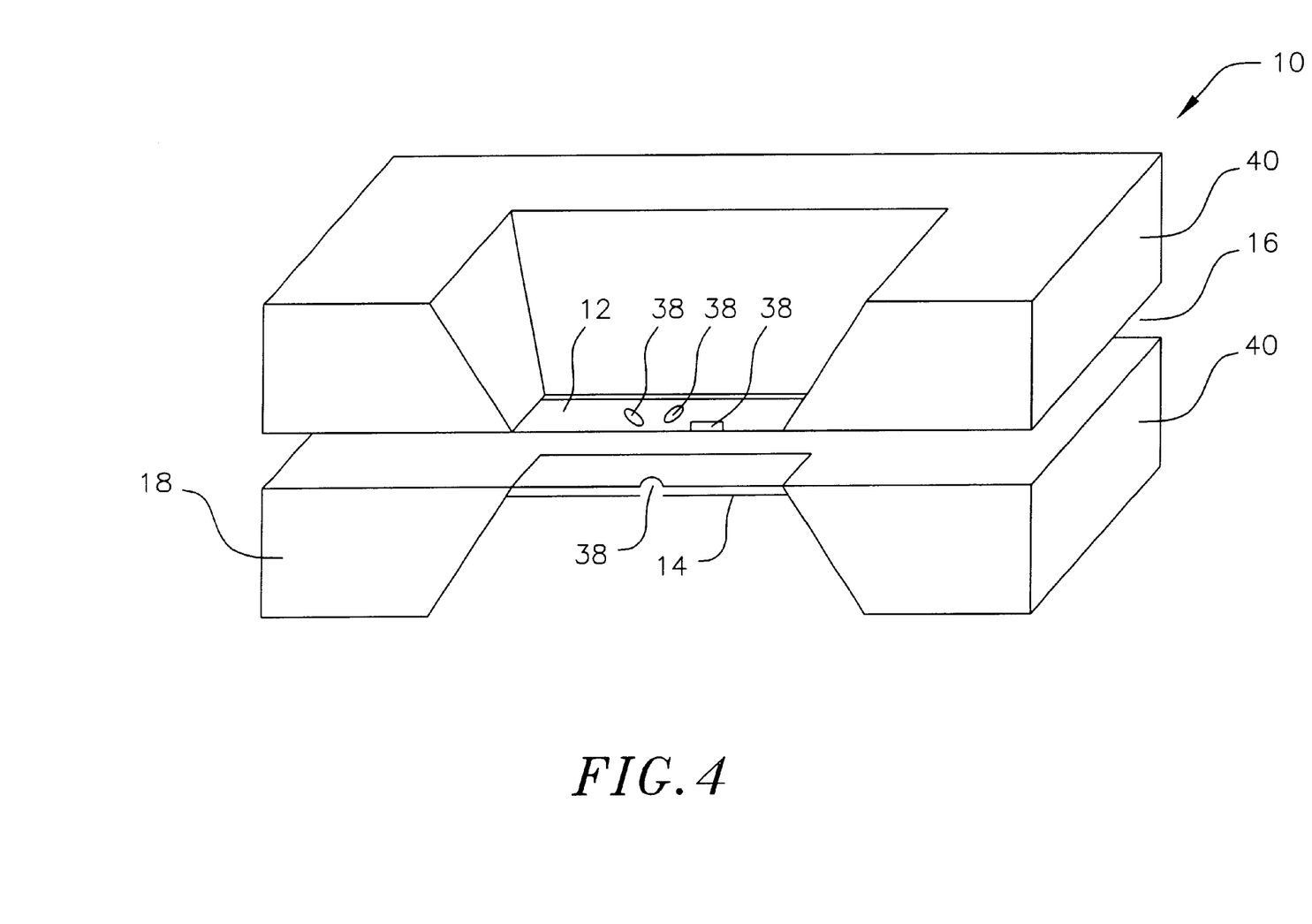
FIG. 4 is a perspective view of the two wafers having perforated diaphragms formed therein positioned to be brought together to form the valve of the present invention.

Once the wafers 18 have been formed they are then sawed into individual chips 40, as shown in FIG. 3 (the holes in the diaphragm are not shown in FIG. 3). In the preferred embodiment of FIG. 4, two chips are ready to be assembled into a valve, while in FIG. 1 these two chips are shown bonded together such that the wafers are attached in a spaced relationship proximate to one another, while the diaphragms 12 and 14 are free to move separately toward and away from each other. The two chips are assembled such that the holes or perforation 38 on the first diaphragm 12 are offset with respect to the holes or perforations 38 of the second diaphragm 14. The conductors 30 on the upper and bottom diaphragm 12 and 14 are shown as Conductor A and Conductor B, respectively, in FIG. 5. Applying a voltage between Conductors A and B generates an electrostatic pressure that causes the diaphragms 12 and 14 to be attracted towards each other to form a tight bond that throttle or impedes the flow of a fluid in the channel 16 between them. In alternative embodiments, magnetic fields or thermally generated forces or bubbles generated by boiling a fluid or a host of other methods can be used to actuate the diaphragms.

Figure 5A:
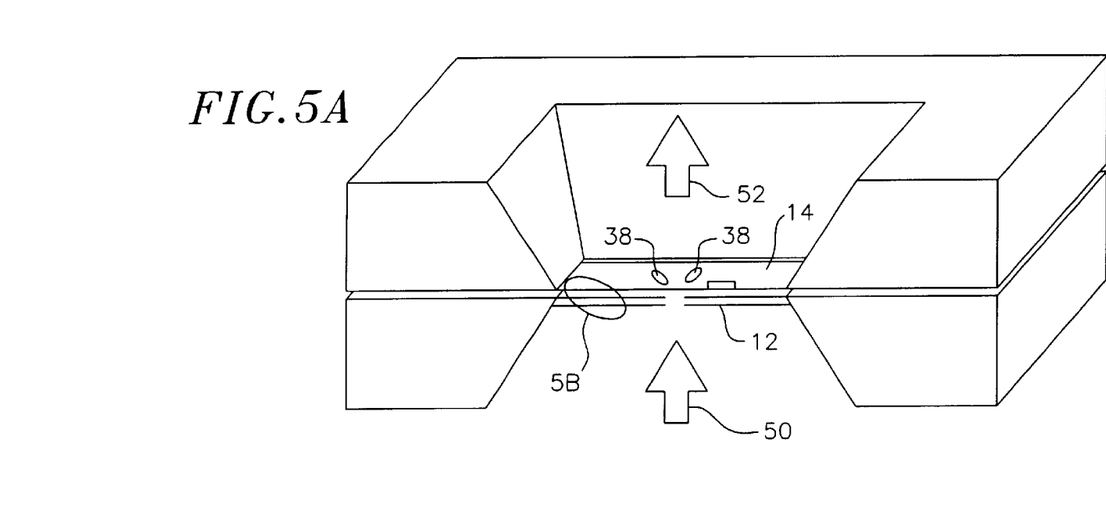
FIG. 5A is a perspective view of a pair of assembled diaphragms to form a valve according to the present invention.
Figure 5B:
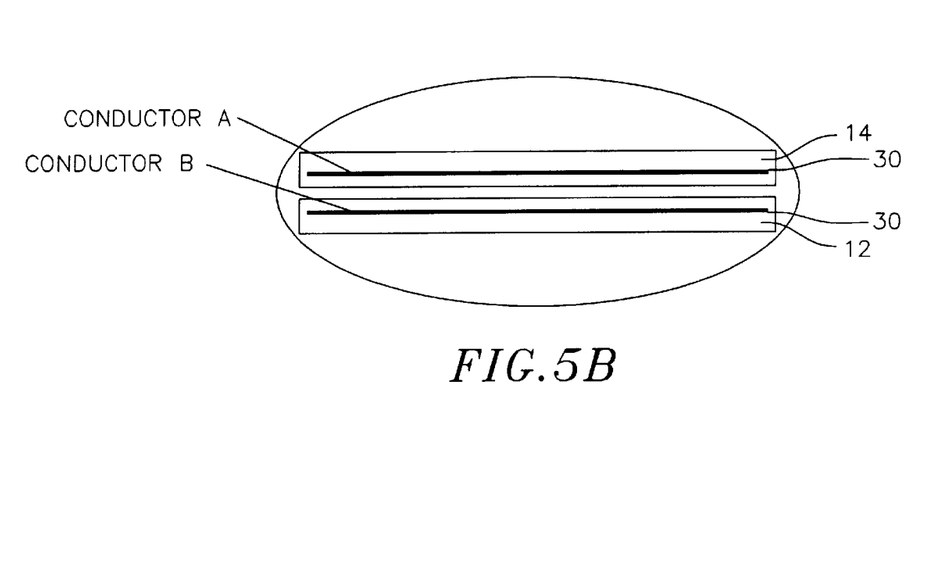
FIG. 5B is a detail fragmentary view of the diaphragms of the valve of FIG. 5A.
Figure 7:
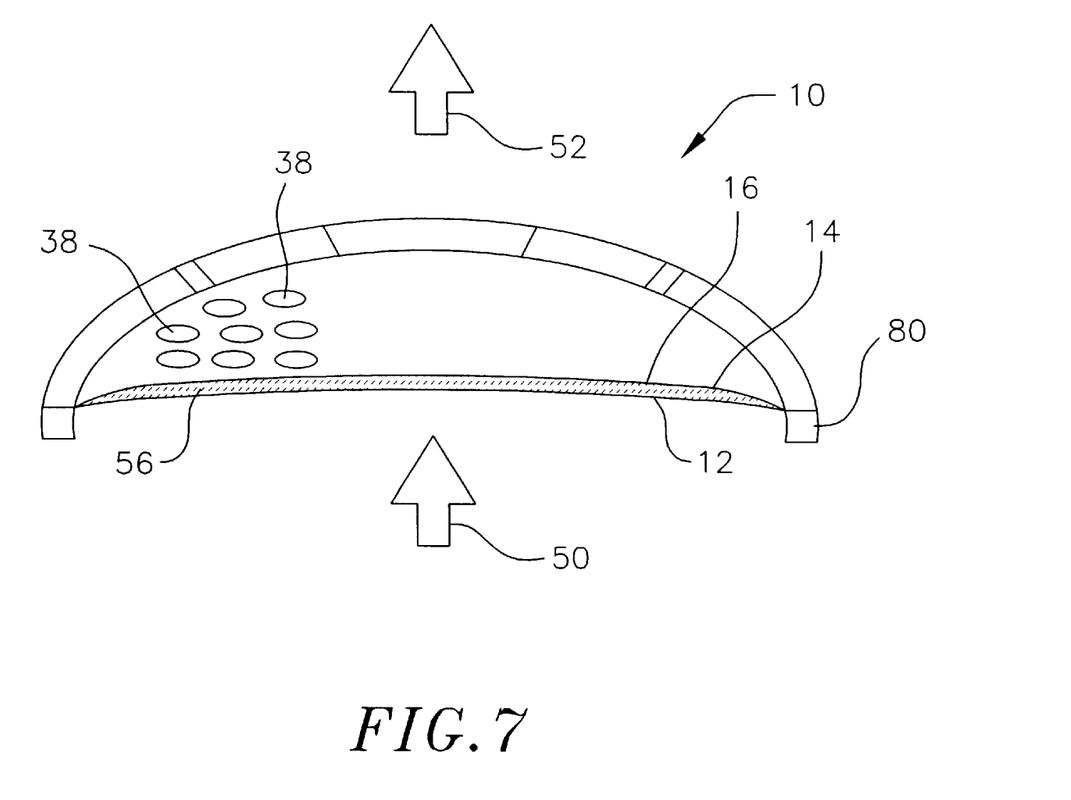
FIG. 7 is a perspective view of an alternative embodiment of the valve according to the present invention.

In operation, as shown in FIGS. 5 and 7, high pressure fluid (depicted by arrow 50) trying to pass through the diaphragms causes both diaphragms to bow away from the high pressure source. The high pressure fluid flows through the holes 38 in the first diaphragm 12 and then must flow between the first and second diaphragms 12 and 14 to reach the holes 38 of the second diaphragm 14, where upon the fluid is free to pass the second diaphragm (depicted by arrow 52). The flow of fluid through the valve can be controlled by applying a voltage to the conductors 30 of the first and second diaphragms, which causes the diaphragms to pull together to stop the fluid flow through the diaphragms. By applying a pressure differential between the two diaphragms, the diaphragms are pulled apart.

An important advantage of the present invention is that a small pressure acting between the diaphragms can control a larger pressure trying to pass through the diaphragms. This is because the larger pressure bows the diaphragms away form the source of high pressure. The energy associated with the high pressure is split between the two diaphragms in an approximately equal manner. To move the diaphragms together to throttle the fluid flow does not require the full pressure applied to the diaphragms, but requires a smaller pressure associated with the small differential motions of the two diaphragms needed to close the valve.

In an alternate embodiment, as illustrated in FIG. 7, a liquid 56, such as air, oil or water, is placed in the channel 16 between the diaphragms 12 and 14. When the two diaphragms are close together, the liquid forms an impenetrable seal that does not leak. When the diaphragms separate, the small amount of liquid between the diaphragms can no longer block the flow of fluid, and there is free passage of fluid through the valve. Because the valve seat is formed by a liquid, it can not be scratched or crushed, and does not deteriorate like conventional valve seats.

In addition, the liquid forming the valve seat interacts with the holes in the diaphragm in a beneficial manner. When the valve is closed, the surface tension between the holes in the diaphragm and the liquid between the diaphragms also inhibits the flow of liquid through the diaphragms. The action of the surface tension causes a hysteresis in the valve that is often beneficial. For example in one valve embodiment there is no actuation. The surface tension of the liquid around the holes in the diaphragm keeps the valve closed until a pre-set pressure, say 10 pounds per square inch or psi, is reached. The valve then opens cleanly and stays open until a lower pressure, say 8 psi, is reached. This valve requires no electronics or sensors or actuation force, instead, the control of the fluid is intrinsic to the design of the valve. In this arrangement, one type of liquid can be used as the seat between the valves, and a second type of liquid used as the medium controlled by the valve, as long as the two liquids have different surface energy properties. For example, if the medium controlled by the valve is air, then liquid used as the seat may be oil.

Figure 6:
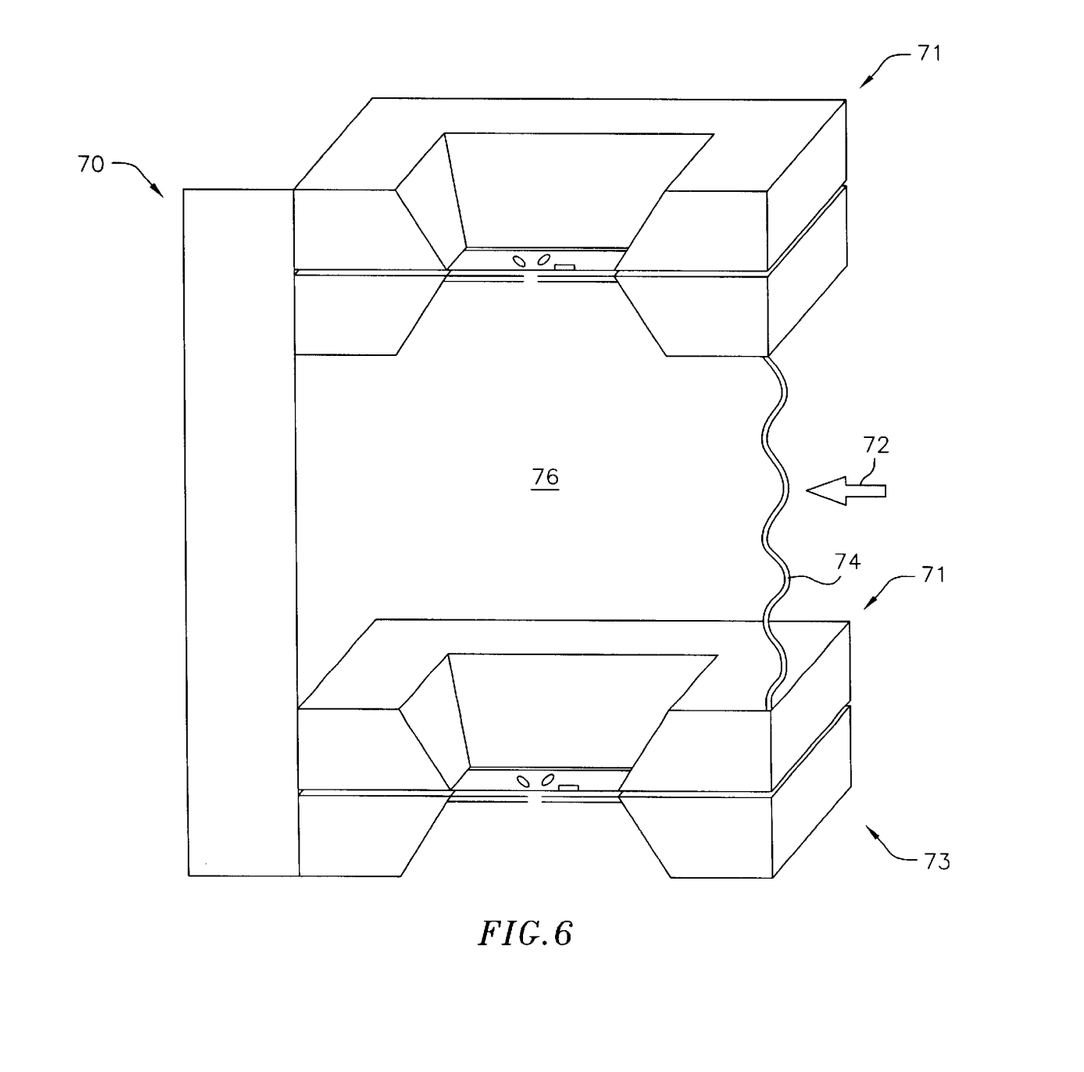
FIG. 6 is a perspective view of two valves according to the present invention assembled in a pump configuration.

In a second embodiment, a pump can be made by attaching two one-way valves 71 and 73 to a variable chamber 70 as shown in FIG. 6. In this embodiment, a variable pumping force (depicted by arrow 72) distends a diaphragm 74 which extends between the two valves to form a volume. When the pumping force pulls the diaphragm in a direction opposite arrow 72, the pressure in the volume drops and fluid is drawn into the volume through valve 71. When the diaphragm is pushed in the direction of arrow 72, the pressure in the volume increases and the fluid flows out of the volume through valve 73. Thus the valves 71 and 73 act as check valves, opening and closing at appropriate times to capture and pressurize fluid.

In a third embodiment, the diaphragms 12 and 14 are made of a flexible sheet film, such as a plastic or epoxy. For example, two thin films of photo sensitive plastic film can be used. The holes 38 in the diaphragms are photolithographically defined, and the two thin films are bonded together on a ring 80 or other suitable substrate which supports the valve in the desired position, as shown in FIG. 7. The thin films may have appropriate conducting and insulating layers to allow electrostatically generated pressures to close the valve. Also, aluminum can be deposited on one side of each film, and covered with an insulator. The two films are then bonded together in the region where the ring support will be attached, such that the aluminum films are innermost and facing each other. Now the photolithography can proceed from opposite sides since the aluminum layer will stop the light that exposes, say the top film, from reaching the bottom film. This method eliminates the need to align the top and bottom film after the holes have been defined.

The present invention has been described in terms of several preferred embodiments. However, the embodiments described above are provided by way of illustration only and should not be construed to limit the invention. Those skilled int the art will readily recognize various modifications and changes that may be made to the present invention without strictly following the example embodiments and applications illustrated and described herein, and without departing from the true spirit of the present invention which is set forth in the following claims.

What is claimed is:

1. A microelectromechanical valve comprising at least two flexible diaphragms in opposed spaced relationship to each other, the diaphragms having offset holes such that fluid flow between the diaphragms is impeded when the diaphragms are in close proximity to one another, and the fluid flow through the diaphragms is enabled when the diaphragms are spaced apart, and an actuator for causing the diaphragms to approach and retract relative to each other.

2. The valve of claim 1 wherein the diaphragms comprise a conductor.

3. The valve of claim 2 wherein the actuator comprises is a voltage applied to the conductors to move the diaphragms towards each other in close proximity.

4. The valve of claim 2 wherein the actuator is a magnetic force.

5. The valve of claim 1 wherein a liquid is disposed between the diaphragms, liquid impeding the flow of fluid through the valve.

6. A microelectromechaincal valve comprising a first diaphragm in spaced opposed relationship to a second diaphragm, the diaphragms being flexible and having offset holes such that fluid flow between the diaphragms is impeded when the diaphragms are in close proximity to one another and fluid flow through the diaphragms is enabled when the diaphragms are spaced apart, and an actuator for causing the diaphragms to approach and retract relative to each other.

7. The valve of claim 6 wherein a liquid is disposed between the diaphragms.

8. The valve of claim 7 wherein the liquid stops the flow of fluid through the valve.

9. The valve of claim 7 wherein surface tension between the liquid and the diaphragms and the diaphragm holes causes a hysteresis in the flow of fluids through the valve.

10. The valve of claim 6 wherein the diaphragms comprise conductors and insulators that enable the generation of electrostatic pressures to close the diaphragms and thus keep the valve closed.

11. The valve of claim 10 wherein facing surfaces of the diaphragms are first covered with a conductor and then an insulator.

12. The valve of claim 10 wherein the conductors on one or both diaphragms are composed of interdigitated fingers that can be separately brought to different voltages.

13. The method of claim 7 where alternating or direct voltages are placed across the interdigitated fingers to cause electrostatic pressures to draw the diaphragms together.

14. The valve of claim 6 wherein the holes may overlap slightly in such a manner that the operation of the valve is still effective, said over lap being due to manufacturing misalignment or deliberate design.

15. The valve of claim 8 wherein the amount of liquid is carefully controlled so that the liquid only blocks the flow of fluid when the diaphragms are adjacent.

16. The valve of claim 7 wherein the liquid is water or other suitable material having a high surface tension.

17. The valve of claim 9 where the size of the holes and the surface tension of the liquid between the diaphragms is carefully controlled to make the valve open and close at specific pressure.

18. The valve of claim 10 wherein the conductors comprise metal such as aluminum or gold.

19. The valve of claim 10 wherein the insulators are thin films selected from a class consisting of silicon nitride or silicon dioxide or glass or thin films of plastic or epoxy.

20. The valve of claim 6 wherein the diaphragms are made of single crystal silicon.

21. The valve of claim 6 wherein the diaphragms are made of material that has been deposited on a silicon wafer.

22. The valve of claim 6 wherein the diaphragms are made of plastic.

23. The valve of claim 7 wherein the first and second diaphragms are made of epoxy.

24. The valve of claim 6 wherein the holes in the diaphragms are photolithographically defined.

25. The valve of claim 6 wherein the separation between the diaphragms is controlled with an electrostatic force.

26. The valve of claim 6 wherein the separation between the diaphragms is controlled with a magnetic force.

27. The valve of claim 6 wherein the separation between the diaphragms is controlled with a piezoelectric force.

28. The valve of claim 6 wherein the separation between the diaphragms is controlled with force generated by thermal expansion.

29. The valve of claim 6 wherein the separation between the diaphragms is generated by a bimorph.

30. The valve of claim 29 wherein the bimorph is actuated with a piezoelectric force.

31. The valve of claim 29 wherein the bimorph is actuated with a thermally generated force.

32. The valve of claim 6 wherein the separation between the diaphragms is controlled by generating a bubble.

33. The valve of claim 32 wherein the bubble is generated thermally.

34. The valve of claim 32 wherein the bubble is generated by electrolysis.

35. The valve of claim 6 wherein the diaphragms are designed such that the fluid pressure exerted on the valve distends both diaphragm at approximately equal amounts.

36. The valve of claim 30 wherein the diaphragms are designed so that small forces can open and close the valve even though large pressures have been applied to the valve.

37. The valve of claim 6 wherein there are three or more diaphragms.

38. The valve of claim 6 wherein the diaphragms have an undulating shape.

39. The method of claim 6 wherein the diaphragms are made of a material that can change its material properties.

40. The valve of claim 39 wherein the diaphragms change their Young's modulus of elasticity to effect the opening and closing of the valve.

41. The valve of claim 39 wherein the diaphragms are made of a material that changes its dimensions when excited by an external agent.

42. The valve of claim 41 wherein the diaphragms are made of a piezoelectric material that changes its dimensions when excited with an electric field.

43. The valve of claim 41 wherein the diaphragms are made of a magnetorestrictive material that changes its dimensions when excited with a magnetic field.

44. The valve of claim 6 wherein the diaphragms are made of a Shape Memory Alloy material that changes dimensions when heated or cooled.

45. The valve of claim 6 wherein one or both of the diaphragms have several stable mechanical configurations, and can be mechanically switched between these mechanically stable configurations to effect the opening and closing of the valve.

46. The valve of claim 6 wherein two valves are used to make a pump.

47. The valve of claim 46 wherein the two valves are connected to a variable chamber.

48. The valve of claim 47 wherein the variable chamber is acted upon by a force that changes the volume of the chamber.

49. The valve of claim 48 wherein the valves open and close in such a manner to enable the pumping of the fluid.

50. The valve of claim 48 wherein the valves open and close in such a manner to enable the pressurizing of the fluid.

51. The valve of claim 48 wherein the force is electrostatic.

52. The valve of claim 48 wherein the force is magnetic.

53. The valve of claim 48 wherein the force is piezoelectric.

54. The valve of claim 48 wherein the force is thermally generated.

55. The valve of claim 48 wherein the force is generated by a Shape Memory Actuator.

56. The valve of claim 48 wherein the force is generated by boiling a liquid.

57. The valve of claim 48 wherein the force is generated by accelerations of the valve assembly.

58. The valve of claim 48 wherein the force is generated by changes in ambient pressure.

59. The valve of claim 6 wherein the diaphragms and associated holes are defined photolithographically.

60. The valve of claim 6 wherein the diaphragms are made using silicon surface micromachining.

61. The valve of claim 6 wherein the diaphragms are made using silicon bulk micromachining.

62. The valve of claim 6 wherein the diaphragms are made using plating technology.

63. The valve of claim 6 wherein the diaphragms are made using molding technology.

64. The valve of claim 6 wherein the diaphragms are made using Electro Discharge Machining.

65. The valve of claim 6 wherein the diaphragms are made by depositing layers containing a solvent that evaporates.

66. A method of controlling fluid flow comprising the steps of:

providing a first diaphragm having a first conductor and a first set of holes;

providing a second diaphragm having a second conductor and second set of holes that are offset relative to the first set of holes, the second diaphragm being in opposed spaced relation to the first diaphragm to form a channel; and supplying pressurized fluid to the first diaphragm;

applying a voltage to the diaphragms to generate an electrostatic force which cause the diaphragms to move together in close proximity, wherein the fluid flow through the diaphragm is impeded due to the close proximity of the diaphragms;

supplying pressure between the diaphragms to cause the diaphragms to retract from each other, enabling fluid flow through the diaphragms.

67. The method of claim 66 further comprising the step of inserting liquid between the first and second diaphragms.

68. A method of making a diaphragm comprising the steps of:

providing a wafer having a first surface and a second surface;

oxidizing the wafer and applying a layer of photoresist to the first and second surfaces;

applying a mask to the first and second surfaces and etching away the photoresist from the first and second surfaces to creates a plurality of openings;

diffusing resistant material into the first surface to create an etchant impermeable layer along the first surface; the first surface only being diffused where the where the photoresist is etched away;

depositing a conductive layer over the layer of photoresist on the first surface;

applying a second layer of photoresist on the conductive layer;

etching the a central region of the wafer and the first surface with an etchant to produce a cavity that extends from the second surface to the interior of the first surface to form a diaphragm having a plurality of holes therein, the diaphragm comprising the conductive layer and the second layer of photoresist.

* * * * *